(12) United States Patent
Bunt et al.

(10) Patent No.: US 6,450,991 B1
(45) Date of Patent: Sep. 17, 2002

(54) DELIVERY DEVICES AND THEIR USE

(75) Inventors: Craig Robert Bunt; Michael John Rathbone; Shane Burggraaf, all of Hamilton (NZ)

(73) Assignee: Interag, Hamilton (NZ)

( * ) Notice: Subject to any disclaimer, the term of this patent is extended or adjusted under 35 U.S.C. 154(b) by 0 days.

(21) Appl. No.: 09/554,603

(22) PCT Filed: Dec. 2, 1998

(86) PCT No.: PCT/NL98/00176

§ 371 (c)(1),
(2), (4) Date: Jul. 14, 2000

(87) PCT Pub. No.: WO99/29259

PCT Pub. Date: Jun. 17, 1999

(30) Foreign Application Priority Data

Dec. 5, 1997 (NZ) .............................................. 329338

(51) Int. Cl.⁷ ............................................. A61M 37/00
(52) U.S. Cl. ..................... 604/143; 604/141; 604/891.1
(58) Field of Search ................. 604/140, 141, 604/143, 145, 890.1, 891.1

(56) References Cited

U.S. PATENT DOCUMENTS

| | | | |
|---|---|---|---|
| 4,564,363 A | 1/1986 | Bagnall et al. ............. 604/891 |
| 5,135,499 A * | 8/1992 | Tafani et al. ................ 604/141 |
| 5,162,116 A * | 11/1992 | Shepherd ..................... 424/438 |
| 5,198,222 A | 3/1993 | Scully et al. ................ 424/438 |
| 5,308,348 A | 5/1994 | Balaban et al. ............. 604/892 |
| 5,318,557 A | 6/1994 | Gross .......................... 604/891 |
| 5,354,264 A | 10/1994 | Bae et al. ...................... 601/21 |
| 5,527,288 A | 6/1996 | Gross et al. ................. 604/140 |
| 5,848,991 A * | 12/1998 | Gross et al. ................. 604/140 |

FOREIGN PATENT DOCUMENTS

WO   WO95/13760   5/1995

* cited by examiner

*Primary Examiner*—Gregory Huson
*Assistant Examiner*—Huyen Le
(74) *Attorney, Agent, or Firm*—Jacobson Holman, PLLC

(57) ABSTRACT

A device for actively releasing material(s) (e.g. intra ruminally) having a plurality of dispensing reservoirs. Each electrolytic cell is capable upon energization under the control of a microprocessor after initiation of generating a gas which will cause (e.g. through action on a piston) by displacement of the material(s) of its respective reservoir sufficient displacement of or change to closure means of that reservoir thereby to allow release of the material(s).

18 Claims, 5 Drawing Sheets

FIG. 5
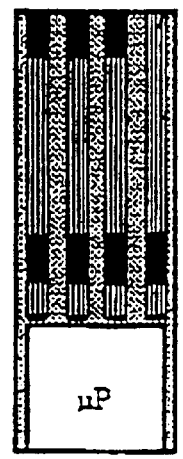
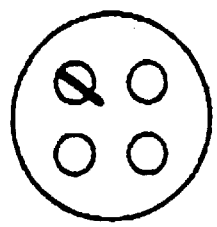
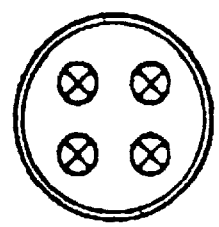
FIG. 6  FIG. 7
FIG. 9
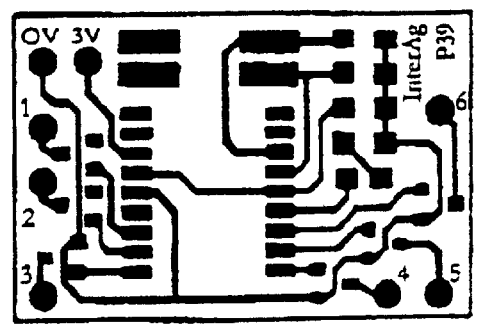

DELIVERY DEVICES AND THEIR USE

TECHNICAL FIELD

The present invention relates to improvements in and/or relating to delivery devices and their use.

Delivery devices such as those utilised to deliver medicaments, supplements and/or other agents into a body cavity (eg; vagina, rumen, etc). Delivery of substances into the rumen of a ruminant whilst a delivery device is retained in the rumen is well known.

BACKGROUND OF THE INVENTION

Generally such intra ruminal devices take the form of a device or bolus capable of being inserted into the rumen by an appropriate applicator to be retained over at least the delivery period by either (a) retention means of variable geometry, e.g. deployable wings or the like, or (b) retention means reliant upon density.

Known for ruminal delivery are devices capable of providing either a continuous (even if not strictly constant) or a pulsed delivery. In the later category are such devices as those reliant upon galvanic action to provide periodic exposure to a fresh reservoir of the dry or fluid composition of or containing the agent to be released.

Agents to be delivered into a ruminant intra ruminally are well known. Their function ranges from that of providing protection against bloat, agents to render more efficient the uptake of food, agents adapted to deal with mineral or vitamin deficiencies, agents to deal with attacks by pests (whether internal or external, etc).

The present invention relates to an active device which does not rely upon the environmental conditions of the device within the rumen of an animal once administered and which is active in a controlled way in its release profile.

Devices of this type are known. For example, in U.S. Pat. No. 4564363 of Smith Kline Beecham Corporation (the full content of which is hereby here included by way of reference) there is disclosed a multi reservoir bolus type device providing for a delayed release of the contents of at least one reservoir under the control of an electrically detonatable squib.

The present invention relates to a device of this kind having a plurality of separately controllable dischargeable reservoirs in a device which is either a density or variable geometry type retention device for intra ruminal insertion.

It is an object of the present invention to provide a viable body cavity delivery device (eg; intra ruminal bolus or device) capable of timed release of multiple reservoirs of agent to be released (whether the same or different) and irrespective of whether or not such quantities to be released at different times are the same or different or are to delivered at different rates or in different quantities. An alternative object is to at least provide the public with a useful choice in respect of active release devices for body cavity (eg; the rumen) insertion. A still other object is to provide a squibless active delivery system.

BRIEF SUMMARY OF THE INVENTION

Accordingly in a first aspect the present invention consists in a device for actively releasing material(s) intra ruminally comprising or including a housing having a plurality of reservoirs each having an outlet from said housing, material(s) to be released in each of said reservoirs, closure means for at least some of said outlets to protect the material(s) from passive release, an electrolytic cell for each of said reservoirs having closure means, each electrolytic cell being capable when activated of generating a gas which will cause by displacement of the material(s) of its respective reservoir sufficient displacement of or change to the closure means of that reservoir thereby to allow release of the material(s), and means to activate selectively each electrolytic cell.

Preferably the device is an intra ruminal device.

Preferably said electrolytic cell of each reservoir is capable through the generation of the gas of expressing at least some of the material(s) out of the outlet of the reservoir.

Preferably the gas of at least some reservoir acts indirectly on the material(s).

Preferably the gas of at least one reservoir acts of material displacement means selected from (i) a piston or plunger arrangement, and (ii) a collapsible bladder or deformable membrane type arrangement.

Preferably said means to activate selectively each electrolytic cell includes a timer and/or logic means capable of delaying the activation of at least one of the electrolytic cells to thus delay the active release of the materials.

Preferably at least one of said closure means is a cap or the equivalent.

Preferably at least one of said closure means is tethered to said housing.

Preferably a film or foil material, or laminate thereof, provides, at least in part, a closure means for at least one of said reservoirs.

Preferably said film or foil is rupturable to allow the active release of the material(s) of the respective reservoir.

Preferably said electrolytic cell of at least one of said reservoirs is capable of being activated so as to provide a timed release of the materials within the respective reservoir.

Preferably said battery is capable of powering the electrolytic cells.

Preferably a switch is provided to energise the device whereupon, at an appropriate time or times, at the control of said means to activate each electrolytic cell, there is an appropriate energising of a particular electrolytic cell and thereafter the active release of the material(s) of the particular reservoir.

Accordingly in another aspect the present invention may broadly be said to consist in an intra ruminal device consisting of, comprising or including a housing having a plurality of reservoirs each having an outlet from said housing, closure means for at least some of said outlets, material(s) to be released from each reservoir in each of said reservoirs, material displacement means to reduce the volume of each such reservoir, such material displacement means being selected from (i) a piston or plunger arrangement, and (ii) a collapsible bladder or deformable membrane type arrangement, electrolytic cells, each dedicated to one of said reservoirs, and each positioned to generate, when activated, a gas which by action on said material displacement means will cause the closure means of its reservoir to allow access of the material(s) (in use) to ruminal fluids(s) and/or membrane(s), and means to activate selectively each electrolytic cell.

Preferably said means to activate selectively each electrolytic cell includes a timer and/or logic means capable of delaying the activation of at least one and preferably several of the electrolytic cells to thus delay the active release of the materials into the rumen (in use) of the respective reservoirs.

Preferably a piston or plunger arrangement is provided in each reservoir and each reservoir is in the form of a barrel of any appropriate cross section for the piston or plunger. Preferably however the cross section is circular.

Preferably the closure means is rupturable or sufficiently movable or deformable at said outlets by the material or materials of the particular reservoir under the action of gas on its material displacement means to achieve the release effect of the hitherto at least substantially sealed material(s).

Preferably said device includes as part of said means to activate a battery capable of powering the electrolytic cells.

Preferably a switch is provided to energise the device whereupon at an appropriate time or times, at the control of said means to activate each electrolytic cell, there is an appropriate energising of a particular electrolytic cell and thereafter the active release of the material(s) of the particular reservoir.

Preferably the arrangement involves the provision of at least one reservoir which substantially immediately makes its materials available (irrespective of whether or not its reservoir requires closure means to be dislodged, ruptured or otherwise affected and irrespective of whether or not there is any active release from such a reservoir under the action of a said material displacement means).

Preferably rumen retention has (i) a density which will result in rumen retention, (ii) a variable geometry retention configuration, or (iii) or both (i) and (ii).

In yet a further aspect the present invention consists in an intra ruminal device consisting of, comprising or including means (for example, a housing) defining a reservoir having an outlet, said reservoir being of a kind which will allow the movement of plungers or pistons towards and out of said outlet, a plurality of separate plungers or pistons positioned at different position from said outlet, material(s) to be released interposed between each of said plungers or pistons within parts of said reservoir, an electrolytic cell capable of generating a gas when activated to cause movement of the assemblage of materials and plungers or pistons to said outlet, and means to activate said electrolytic cell, the construction and arrangement being such that after intra ruminal insertion of the device, the means to activate said electrolytic cell can present serially the different masses of the materials within the reservoir to or into the rumen, a plunger or piston being discharged from the outlet prior to presenting for release the next mass of material to be serially presented.

Preferably said means to activate is of a kind previously described.

Preferably the arrangement is substantially as hereinafter described.

Preferably said device (in any of its forms) is of a variable geometry retention kind.

Preferably said means to activate each or the electrolytic cell can likewise activate a release mechanism for the variable geometry means so that the device after such activation (which is after the release of at least substantially all of the materials desired) can be discharged from the rumen by the ruminant into whom it has been inserted.

Preferably said variable geometry means is affected by a squib.

In still other variants a weighting device can be disassociated under the action of such means to activate so as to render parts of the original device thereafter dischargeable from the rumen under the action of the ruminant.

In a further aspect the present invention consists in insitu, in the rumen of a ruminant, a device as previously defined.

In still a further aspect the present invention consists in a method of delivering a substance into the rumen of an animal which comprises locating a device in accordance with the present invention in the rumen of the ruminant, the device having been initiated (for example by activation of a switch or otherwise) so that a sequence of material/substance release thereafter results.

In a further aspect the present invention consists in the use intra ruminally of a device in accordance with the present invention.

Preferred forms of the present invention will now be described with reference to the accompanying drawings in which;

FIG. 1 shows a device for the time delivery of an active agent, the device being of a density type retention device and having multiple barrels (preferably circular) with the material to be released from each barrel being protected by a seal [e.g. of a foil or other material, (e.g. a suitable wax)], FIG. 2A shows a variable geometry version of the device, the device having means providing retention wings which for the purpose of insertion would be configured as is known in the art but which deploy after ruminal insertion, the device having provision for separating the wings from the remainder of the device to thus allow its expulsion by an animal from its rumen, FIG. 2B is a view A—A of FIG. 2A, FIG. 3 is still a further variant of a device in accordance with the present invention (this time shown as a density type device but again, as with the device of FIG. 1, being one to which, if desired, variable geometry means could be attached), FIG. 4 shows a release profile according to some predetermined program for devices such as depicted in FIGS. 1 through 3 showing a delay on first activation and a periodic release of at least two subsequent reservoirs/barrels, FIG. 5 is a diagrammatic side elevation of a plunger provided series of reservoirs some of which are sealed by closure means in the form of a bung and one of which is sealed solely by a film or foil or lamination thereof, FIG. 6 is a top view of an arrangement as shown in FIG. 5 showing how, if desired, at least one bung can be tethered to the housing which defines the multiple reservoirs, FIG. 7 is a similar view to that of FIG. 6 but showing how frangible regions can be provided to allow selective rupture, FIG. 8 is a diagram showing a preferred circuit, and FIG. 9 shows an enlarged layout as might used utilised for a circuit as shown in FIG. 8.

DETAILED DESCRIPTION

In accordance with the present invention reference is made to U.S. Pat. No. 5,527,288 and 5,318,557 of Elan Medical Technologies Limited which show the utilisation of an electrolytic cell capable of generating gas under an electric current.

Reference is also made to U.S. Pat. No. 5,354,264 of Insutech Inc which discloses a drug delivery device which utilises gas pressure from free oxygen and hydrogen derived from the electrolysis of water at the electrodes in negatively charged polymeric hydrogels by electro-osmosis. In U.S.

Pat. No. 5,354,264 there is described the use of that gas pressure to force the infusion of drugs through appropriate means into the body.

The present invention recognises a desire to provide periodic availability of stored materials in a rumen retainable device and to make different quantities of the material available at different times for assimilation by the animal into which the device has been inserted.

FIGS. 1 and 2 (i.e. 2a and 2B) show devices of same type, i.e. individual barrels from which the materials to be discharged can be selectively released.

Referring to FIG. 1 there is shown for each barrel or reservoir a retained quantity of substance or material 1 to be released and an outlet at 2 which is sealed by a rupturable foil 3. Other forms of closure means can be utilised, for example, wax or a plug. Indeed FIG. 2 shows plug like members 4 which can, if desired, be an appropriate wax.

Within each of the barrels is shown a plunger or piston 5. Positioned in or communicable with each barrel behind the plunger 5 in the barrel in each instance is the electrolytic cell 6 with its electrodes.

Each electrolytic cell is connected to activating means which includes an electronic control unit 7, a battery 8 and a switch 9.

The version shown in FIG. 2 is provided with wings 10 capable under the control of the electronic control unit 7 of activating a squib or other means 11 (it could even be a similar electrolytic cell) to discharge the deformable variable geometry wing defining member 10 from the remainder of the device to thus allow expulsion of the residual components from the rumen. Not shown is the density version which may likewise discharge a weight using a similar mechanism.

The release profile envisaged with such a device is along the lines shown in FIG. 4.

FIG. 3 shows a different variant of the present invention where there is a single barrel having separated quantities in the barrel of the material 1 to be released. In this form a series of interposing plungers or pistons 4 are provided to interpose between the separate quantities and preferably also a seal 12.

In this form of the present invention a single large electrolytic cell 6 is utilised but is activated selectively so as in series and over selected time periods (i.e. by the generation of still more gas to add to that already generated and still trapped) to dislodge that member 5 in advance of the next quantity of materials to be released 1. A profile again of the kind envisaged in FIG. 4 is achievable.

FIG. 5 shows a side view of a preferred form of device having, by way of example, four reservoirs. Three are provided with a bung or the like preferably overlaid by a sheet of rupturable material, one of the devices is shown without a bung as that preferably as the first to discharge its material upon insertion.

In each instance as shown in FIG. 5 a piston is provided to cause the discharge of the contents.

FIG. 6 shows a top view of a device such as that shown in FIG. 5 showing how if desired one or more of the bungs can be tethered to the top of the housing.

FIG. 7 shows how a rupturable laminate may overlie the arrangement of, for example, FIG. 6.

In use therefore an aluminium foil of a configuration such as FIG. 7 may be laminated over the openings to the reservoirs and marked in such a manner that rupture occurs by the action of the reservoir contents being expelled. This is irrespective of whether or not any bungs are used instead of or under the rupturable laminate.

The contents of the reservoirs may be expelled under the influence of an electronic microprocessor and feedback mechanism. Sensors external to the device may upon the detection of a predetermined marker activate electrolysis and expel the content of the reservoir.

Further feedback mechanism may act to terminate, decrease the rate, increase the rate or extend electrolysis upon determining a particular parameter value, for example,

| Parameter | Response |
| --- | --- |
| reservoir has not released contents after appropriate time has passed | increase rate or duration of electrolysis |
| sufficient electrolysis has occurred to open reservoir closer | terminate or decrease rate of electrolysis |
| metabolite or biological marker detected | initiate electrolysis to expel contents of reservoir |
| metabolite or biological marker detected | terminate electrolysis to retain contents of reservoir |

Figure 1:
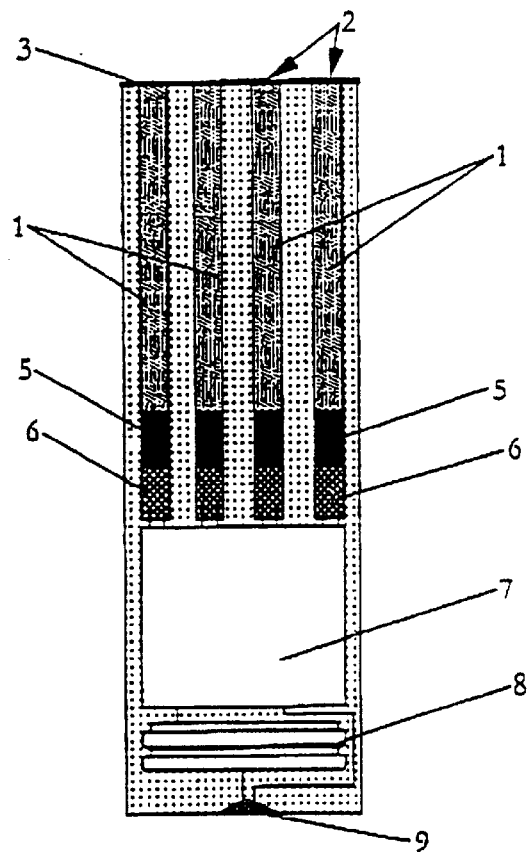
Figure 2A:
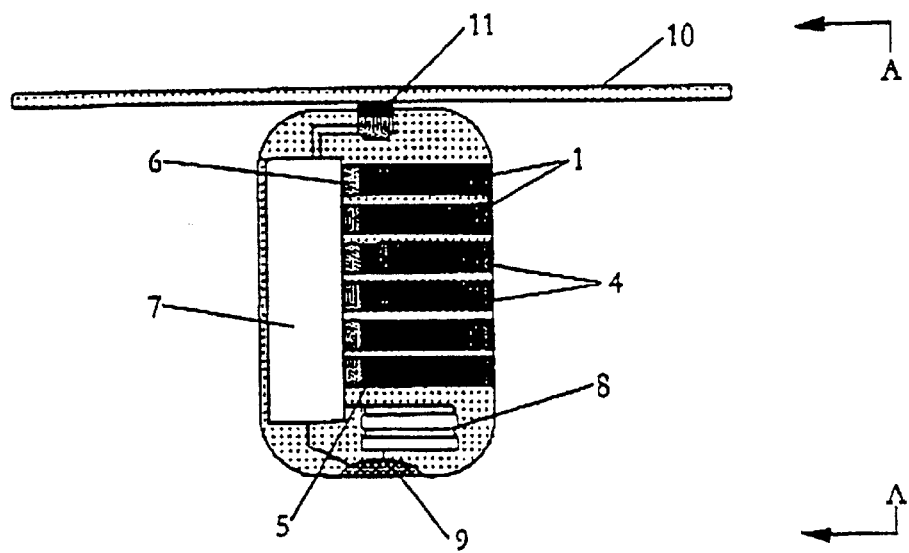
Figure 2B:
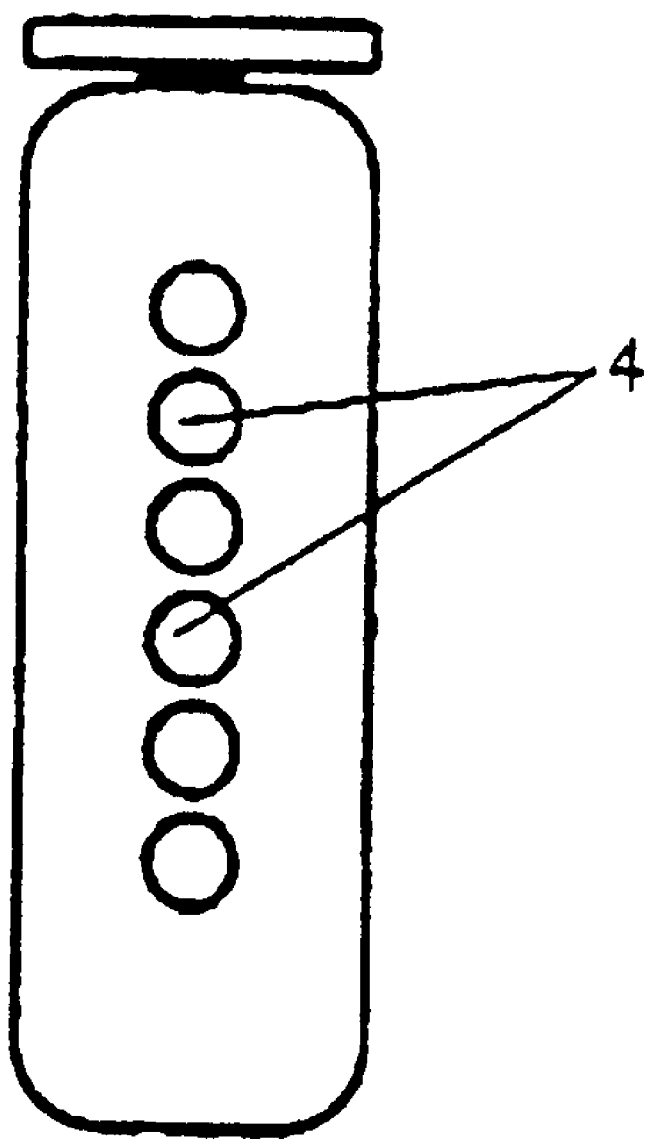
Figure 3:
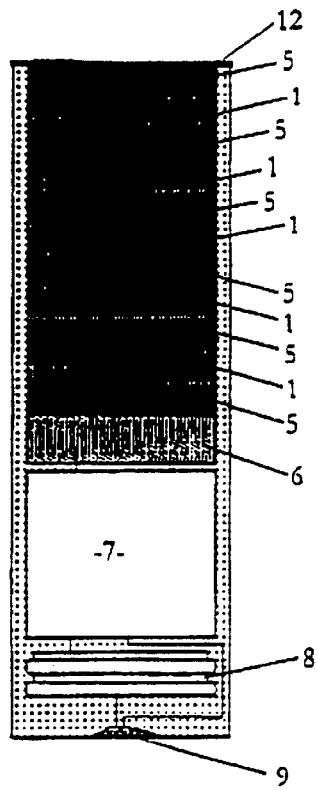
Figure 4:
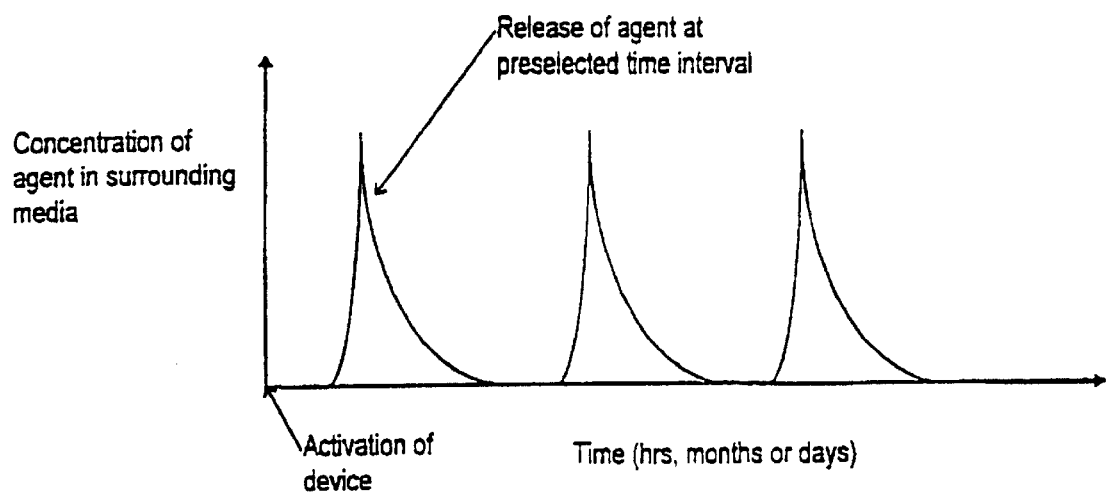
Figure 8:
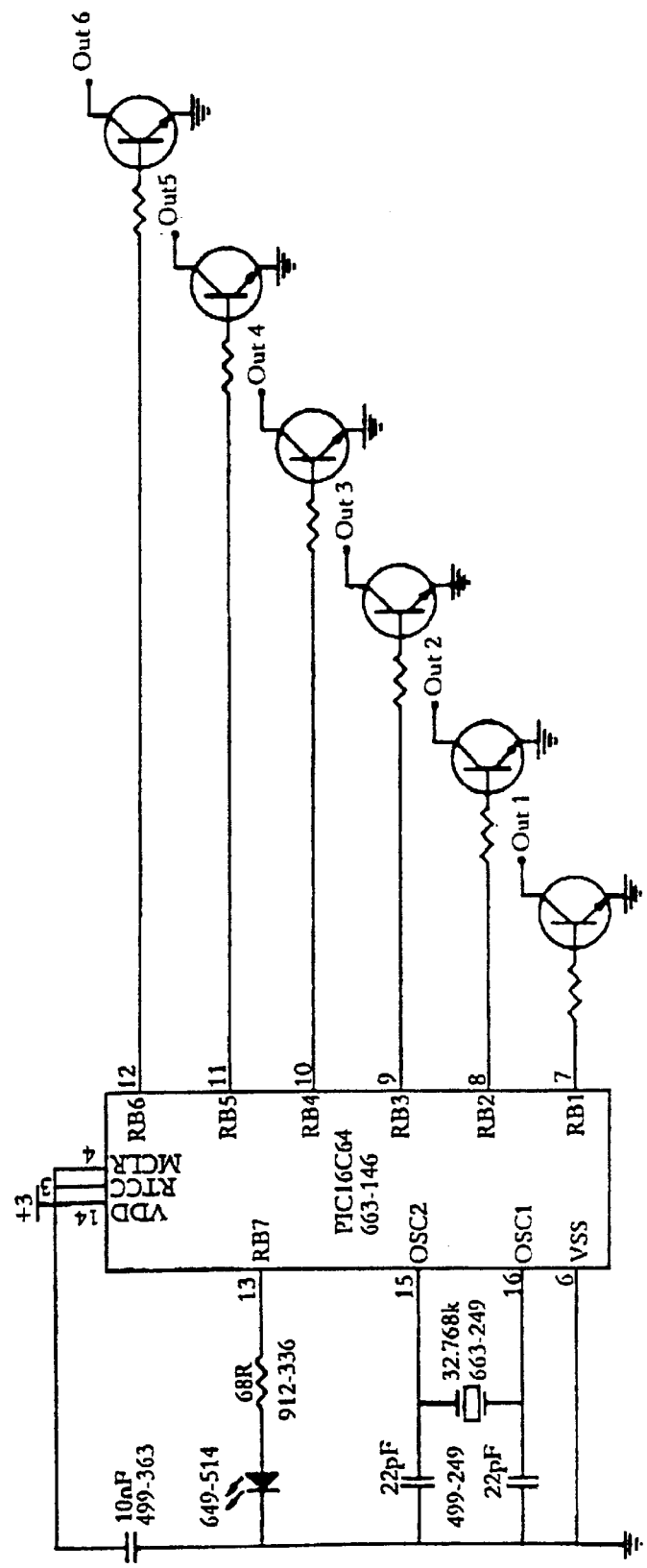

FIG. 8 shows a preferred circuit for a transistor and resistor housed in a single SOT-23 package (DTC114T "Digital Transistor"—Farnell 662-781).

The circuit utilises a PIC16C54A—04/SO Microprocessor to provide the control mechanism for the hydrogel cells.

Specifically it is used to generate the activation sequence, timing and the rate of gas production in each cell.

Two 3V batteries provide the power source for the circuit.

The microprocessor is powered from one 3V battery.

Each output switches 6V to the e-gel cell via a digital transistor DTC114T (base resistor and transistor in same package).

An LED is used to provide visual indication of the circuit's operation.

The circuit uses a 32.768 kHz crystal oscillator. The timing delays are generated from this clock source.

An external resistor may be used to limit the current flowing to the hydrogel cell and thereby limit the rate of gas production.

When the circuit is powered up (from an external switch) the LED flashes 10 times to indicate that the circuit is active.

After a programmed delay one (or more) of the outputs is switched on for a programmed time, after which the output may be turned off.

Each output consists of six transistors, switching 6V to the hydrogel cells. Each e-gel cell may be connected to more than one transistor output.

Each time an output is switched on, the LED will flash a programmed number of times to indicate that an output circuit has been activated.

At the end of the routine, the microprocessor loops (ie; does nothing) until its battery is exhausted.

The program may be modified to suit a specific number of outputs (e-gel cells) or required timing delays.

FIG. 9 shows one suitable microprocessor board arrangement for such a device (enlarged 2:1).

It is believed that devices in accordance with the present invention will find widespread acceptance.

What is claimed is:

1. A device for actively releasing material(s) comprising or including a housing having a plurality of reservoirs each having an outlet from said housing, material(s) to be released in each of said reservoirs, closure means for at least some of said outlets to protect the material(s) from passive release, an electrolytic cell for each of said reservoirs having closure means, each electrolytic cell being capable when activated of generating a gas which will cause by displacement of the material(s) of its respective reservoir sufficient displacement of or change to the closure means of that reservoir thereby to allow release of the material(s), and means to activate selectively each electrolytic cell.

2. A device as claimed in claim 1 wherein said electrolytic cell of each reservoir is capable through the generation of the gas of expressing at least some of the material(s) out of the outlet of the reservoir.

3. A device as claimed in claim 1 wherein the gas of at least some reservoir acts indirectly on the material(s).

4. A device as claimed in claim 3 wherein the gas of at least one reservoir acts of material displacement means selected from (i) a piston or plunger arrangement, and (ii) a collapsible bladder or deformable membrane type arrangement.

5. A device as claimed in claim 1 wherein said means to activate selectively each electrolytic cell includes a timer and/or logic means capable of delaying the activation of at least one of the electrolytic cells to thus delay the active release of the materials.

6. A device as claimed in claim 1 wherein at least one of said closure means is a cap or the equivalent.

7. A device as claimed in claim 6 wherein at least one of said closure means is tethered to said housing.

8. A device as claimed in claim 1 wherein a film or foil material, or laminate thereof, provides, at least in part, a closure means for at least one of said reservoirs.

9. A device as claimed in claim 8 wherein said film or foil is rupturable to allow the active release of the material(s) of the respective reservoir.

10. A device as claimed in claim 1 wherein said electrolytic cell of at least one of said reservoirs is capable of being activated so as to provide a timed release of the materials within the respective reservoir.

11. A device as claimed in claim 1 which includes a battery capable of powering the electrolytic cells.

12. A device as claimed in claim 1 wherein a switch is provided to energise the device whereupon, at an appropriate time or times, at the control of said means to activate each electrolytic cell, there is an appropriate energising of a particular electrolytic cell and thereafter the active release of the material(s) of the particular reservoir.

13. A device of claim 1 wherein the device for rumen retention has (i) a density which will result in rumen retention;

(ii) a variable geometry retention configuration, or (iii) or both (i) and (ii).

14. A device of claim 1 for intra ruminal use.

15. The use intra ruminally of a device of claim 1.

16. A method of delivering a substance in to a body cavity of an animal which comprises locating a device as claimed in claim 1 in the body cavity, the device having been initiated so that a sequence of material/substance release thereafter results.

17. A method of claim 16 wherein the body cavity is the rumen of a ruminant.

18. An intra ruminal device comprising or including means defining multiple reservoirs each having an outlet, each said reservoir being of a kind which will allow the movement of plungers or pistons towards the outlet of said reservoir, a plunger or piston positioned in each said reservoir, material(s) to be released interposed between each of said plungers or pistons and the outlet of its reservoir, an electrolytic cell for each reservoir, each cell being capable of generating a gas when activated to cause by action on its plunger or piston movement of the assemblage of material(s) out of said outlet, and means to selectively activate each said electrolytic cell, the construction and arrangement being such that after intra ruminal insertion of the device, the means to selectively activate each said electrolytic cell can present serially the different masses of the material(s) within the reservoirs to or into the rumen.

\* \* \* \* \*